United States Patent [19]

Horrocks et al.

[11] 4,386,078

[45] May 31, 1983

[54] THERAPEUTIC AGENTS FOR PREVENTING PHOSPHOLIPID DEGRADATION AND FREE FATTY ACID PROLIFERATION

[75] Inventors: Lloyd A. Horrocks; Robert V. Dorman, both of Columbus, Ohio; Zbigniew M. Dabrowiecki, Warsaw, Poland

[73] Assignee: The Ohio State University Research Foundation, Columbus, Ohio

[21] Appl. No.: 303,505

[22] Filed: Sep. 18, 1981

Related U.S. Application Data

[63] Continuation-in-part of Ser. No. 126,526, Mar. 3, 1980, abandoned.

[51] Int. Cl.$^3$ .............................................. A61K 31/70
[52] U.S. Cl. .................................................. 424/180
[58] Field of Search ................... 424/180; 536/27, 28, 536/29

[56] References Cited

PUBLICATIONS

M. Martinet et al., "Effects of Cytidine-5 Diphosphocholine on Norepinephrine, Dopamine and Serotonin Synthesis in Various Regions of the Rat Brain (1)".
M. Martinet et al., "Interaction of CDP-Choline with Synaptosomal Transport of Biogenic Amines and Their Precursors in Vitro and in Vivo in the Rat Corpus Striatum," Experientia 34, 1197–1199, (1978).
M. Rigoulet et al., "Unilateral Brain Injury in the Rabbit; Reversible and Irreversible Damage of the Membranal ATPases", J. Neurochem 27, 535–541, (1979).
F. Cohadon et al., "Oedeme Cerebral Vasogemique", Nouvelle Press Medicale, 8 1589–1591, (1979).
F. Boismare et al., "Action of Cytidine Diphosphocholine on Functional and Hemodynamic Effects of Cerebral Ischemia in Cats", Pharmacology 17 15–20, (1978).
Chemical Abstracts, 91, 17553c, (1979).
Manaka, et al., Experientia 30, 179–180, (1974).

*Primary Examiner*—Blondel Hazel
*Attorney, Agent, or Firm*—Millard & Cox

[57] ABSTRACT

Disclosed is a method for substantially maintaining glycerophospholipid production by cells and for suppressing consequent free fatty acid proliferation in said cells wherein injury or disease has caused normal glycerophospholipid production of said cells to become retarded. Such method comprises presenting said cell with CDP-ethanolamine, CDP-N-methylethanolamine, CDP-N,N-dimethylethanolamine, mixtures thereof or mixtures of these compounds with CDP-choline. Injuries or diseases to which the method has applicability include ischemia, heart disease, stroke, and spinal cord injury. The CDP-compounds may be administered either before or after the onset of the injury or disease.

18 Claims, 1 Drawing Figure

THERAPEUTIC AGENTS FOR PREVENTING PHOSPHOLIPID DEGRADATION AND FREE FATTY ACID PROLIFERATION

The invention described herein was made in the course of work under a grant or award from the Department of Health, Education and Welfare.

This application is a continuation-in-part of our co-pending Patent Application Ser. No. 06/126,526 filed Mar. 3, 1980, now abandoned.

BACKGROUND OF THE INVENTION

The present invention relates to the use of cytidine diphospho (CDP) compounds as therapeutic agents for preventing phospholipid degradation, and to compositions containing these compounds.

During investigative studies of CDP-choline and CDP-ethanolamine we discovered that injections of these compounds into normal rat brains increased the radioactivity of cerebral lipids when [$^{14}$C]-linoleic acid was present. These results were interpreted to mean that these CDP compounds could stimulate the incorporation of free fatty acids into cerebral lipids. Since prior work had disclosed that ischemic trauma, such as seen in stroke or heart disease, resulted in free fatty acid proliferation, studies were undertaken to determine the effects of CDP compounds on fatty acid concentrations during cerebral ischemia.

Heretofore, Cohadon et al, "Oedeme Cerebral Vasogenique", *La Nouvelle Press Medicale*, Vol. 8, No. 19, pp 1589-1591 (Apr. 28, 1979) and "Unilateral Brain Injury in the Rabbit: Reversible and Irreversible Damage of the Membranal ATPases", *J. Neurochem.*, 27, 535-541 (1979), report that during vasogenic cerebral edema there is an impairment of mitochondrial ATPase and of Na/K/ATPase. This impairment is speculated to be related to the phospholipid environment in the brain. Use of CDP-choline is noted to be mildly capable of correcting this impairment and in reducing the edema. The CDP-choline was administered by intravenous injection 24 hours after a cold injury was inflicted. Studies by Boismare et al, "Action of Cytidine Diphosphocholine On Functional and Hemodynamic Effects of Cerebral Ischemia in Cats," *Pharmacology*, 17:15-20 (1978), on cats that were made hypercapnic and acidotic by strangulation, noted that the amplitude of electrical activity increased more with an intracarotid injection of CDP-choline than without such injection. These authors hypothesize that a metabolic action is exhibited by the drug. In other studies of CDP-choline, Manaka et al, "Mechanism of Action of CDP-choline in Parkinsonism", *Experientia*, 30, pp 179-180 (1974), report that CDP-choline appears to be effective in treating Parkinsonism. Note also that studies on the interaction and effect of CDP-choline on various neurotransmitters have been reported by Martinet et al, "Interaction of CDP-choline with Synaptosomal Transport of Biogenic Amines and Their Precursors in Vitro and In Vivo in the Rat Corpus Striatum", *Experientia*, 34, pp 1197-1199 (1978) and "Effects of Cytidine-5' Diphosphocholine in Norepinephrine, Dopamine and Serotonin Synthesis in Various Regions of the Rat Brain", *Arch. Int. Pharmacodyn*, 239, pp 52-61 (1979).

BROAD STATEMENT OF THE INVENTION

The present invention provides a method for substantially maintaining glycerophospholipid production in cells and for suppressing consequent free fatty acid proliferation in a mammalian cell, said cell being susceptible to an injury to said mammal which cause normal glycerophospholipid production of said cell to become retarded. Such method comprises presenting said cell with a pharmaceutically effective proportion of cytidine diphosphoethanolamine, cytidine diphosphos-N-methylethanolamine, cytidine diphospho-N,N-dimethylethanolamine, or mixtures thereof, or mixtures of at least one of said cytidine compounds with cytidine diphosphocholine.

The invention also provides a therapeutic agent comprising a substantially isotonic, injectable solution containing cytidine diphosphocholine and at least one cytidine compound selected from the group consisting of cytidine diphosphoethanolamine, cytidine diphospho-N-methylethanolamine and cytidine diphospho-N,N-dimethylethanolamine.

DETAILED DESCRIPTION OF THE INVENTION

Figure 1:
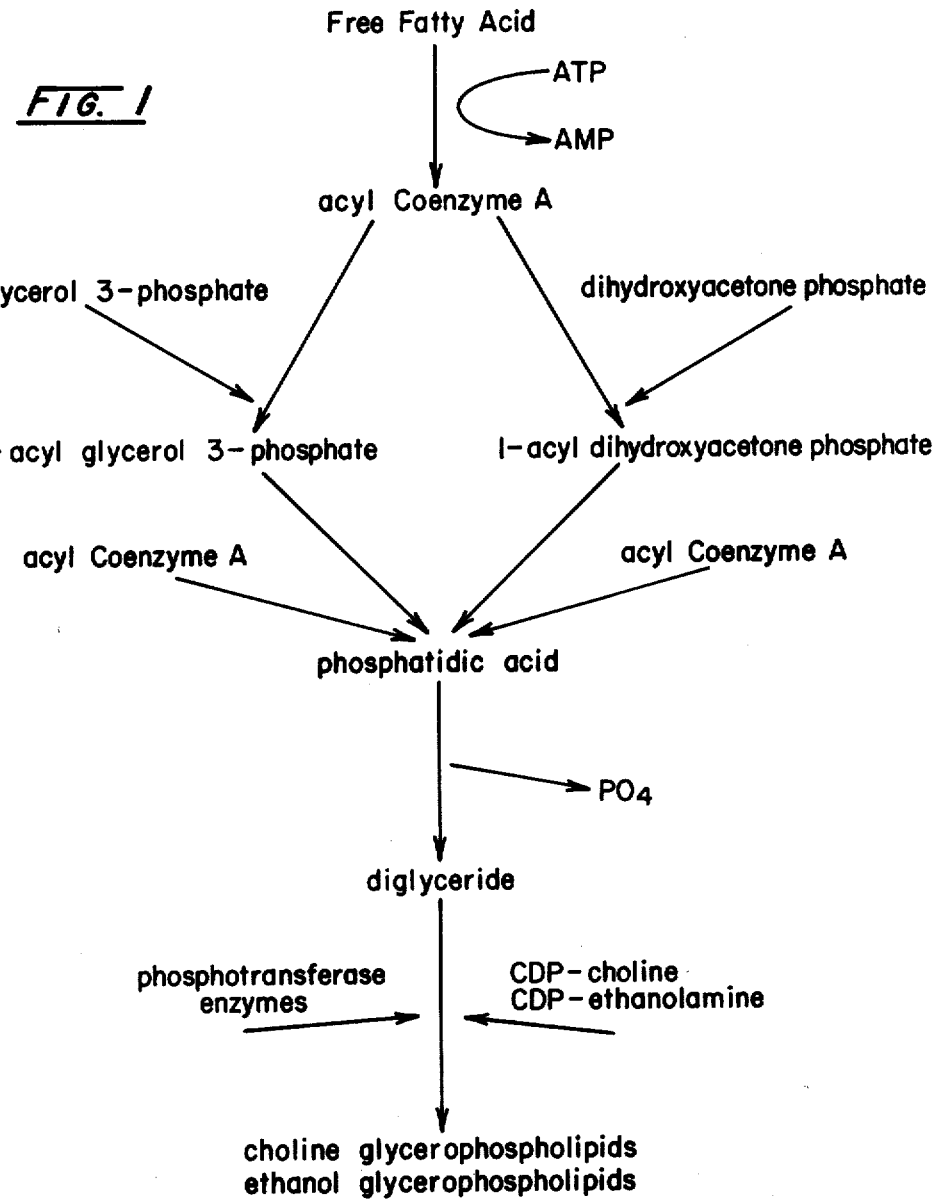

As noted above, the present invention grew out of studies of cerebral tissue subjected to ischemic trauma. While full knowledge of all of the chemical reactions which occur during such ischemia have not been confirmed fully, a great deal of evidence has been uncovered and will be presented herein. Briefly, it is postulated that during ischemia, lipid production is severely suppressed, especially in the cell membranes. Loss of membranous lipids, then, leads to a breakdown of the cell membrane and impairment of the cell which often is totally irreversible. Though a variety of mechanisms for the observed lipid degradation can be envisioned, one mechanism will be offered herein. This mechanism is not fully confirmed and should not be construed as a limitation of the present invention. Of importance in the present invention is that control of lipid degradation has been achieved.

Initially, it is known that free fatty acids can retard mitochondria and, thus, production of ATP (adenosine triphosphates) in the brain. Thus, cerebral tissue is in a lower energy state by virtue of evidenced diminished concentrations of ATP. Note also that ATP is necessary in the synthesis of endogenous CDP-choline and CDP-ethanolamine. Intuitively, then, less choline and ethanolamine lipids would be expected during ischemia. In fact, this has been determined experimentally. Moreover, with the observed lower levels of cerebral lipids, intuitively one would expect lipid-precursors to proliferate or be converted to other compounds. As the examples will demonstrate, free fatty acid proliferation during ischemia has been confirmed. Accordingly, then, it would appear important to control free fatty acid proliferation during ischemia so that the energy state of the cells, e.g. ATP concentrations, could be substantially maintained.

One other hypothesis is that free fatty acid proliferation leads to production of compounds which during ischemia are pathologically undesirable. Such free fatty acid compounds are believed to include peroxides and hydroxylated compounds such as, for example, prostaglandins, thromboxanes, HETE compounds (hydroxyeicosatetraenoic acids,) and the like. Such strongly bioactive compounds, then, may lead to fever, coma, uncontrolled constriction or dilation of blood vessels, uncontrolled aggregation or prevention of aggregation of platelets, and the like. Thus, there may be a double effect with respect to free fatty acid proliferation during ischemia as such excess free fatty acids not only suppress mitochondrial ATP synthesis but also may be converted into compounds which create physiological complications during the ischemia.

As noted above, free fatty acid proliferation and diminished cerebral glycerophospholipid production has been confirmed experimentally in tissue subjected to ischemic trauma. The proposed mechanism which connects these two observations will be described in connection with the drawing for illustrative purposes only and not by way of limitation of the present invention. Such mechanism is postulated to be the normal synthetic activity of cerebral tissue which normally occurs in the cell membrane. Referring to the drawing, the first step in the chain of reactions involves the conversion of a free fatty acid to an acyl Coenzyme A which reaction is initiated by ATP which is converted to AMP thereby. Note that this reaction is an instance of the energy state of the tissue being utilized. Next, the acyl Coenzyme A reacts with glycerol 3-phosphate or dihydroxyacetone phosphate to form 1-acylglycerol-3-phosphate and 1-acyl dihydroxyacetone phosphate, respectively. With the addition of another molecule of the acyl Coenzyme A, the phosphate compounds are converted into phosphatidic acid. Loss of the phosphate anion, $PO_4$, results in conversion of the phosphatidic acid into a diglyceride. Finally, it is postulated that phosphotransferase enzymes metabolize the diglyceride in the presence of CDP-choline and CDP-ethanolamine to produce the desired choline glycerophospholipids and ethanolamine glycerophospholipids, respectively, with CMP by-product resulting thereby. Again, this reaction requires energy from the tissue to be utilized. It should be noted that the phosphotransferase reaction shown in the drawing is reversible.

Since the energy state of the tissue is diminished during ischemia, free fatty acid cannot be converted via the first step to acyl Coenzyme A, thereby reducing the synthetic capacity for acyl Coenzyme A. This would result in free fatty acid proliferation during ischemia. Further, the lower amounts of acyl Coenzyme A would have a rippling or domino effect down the sequence of reactions leading to the conversion of the diglyceride into the desired glycerophospholipids. Thus, lower proportions of glycerophospholipids would be expected during ischemia, because of hydrolysis of the existing glycerophospholipids and reduced synthesis of fresh glycerophospholipids due to lack of CDP-choline and CDP-ethanolamine, and this lowering of glycerophospholipid levels has been confirmed experimentally. Although it might be expected that CDP-choline and CDP-ethanolamine levels would also drop during ischemia, in practice these levels are found to rise, presumably because the normal action of phosphotransferases is reversed during ischemia. It is believed that diglyceride may be proliferated during ischemia too, though this is believed to not necessarily contribute to damage of the tissue since it is believed that the diglyceride proliferation causes aggregation of enzymes which are responsible for its conversion into lipids. Thus, it is believed that the diglyceride stimulates its own incorporation into the lipids and is self-regulating thereby.

The effect of presenting an excess of an exogenous CDP-amine compound to the tissue during ischemia is to shift the equilibrium of the entire process towards the synthesis of the phospholipids. Free fatty acids are incorporated into lipids under normal conditions at a time when they are being released from the lipids. Thus, by injecting the CDP-amine compounds into the tissue, normal synthetic activities can be substantially maintained even when the energy state of the tissue is diminished.

Although preliminary experiments indicated that both CDP-choline and CDP-ethanolamine were effective in maintaining glycerophospholipid production and for suppressing free fatty acid proliferation in mammalian cells, more refined analysis of the effects of CDP-choline and CDP-ethanolamine on the various groups of fatty acids present in the cell indicates (as reported in more detail below) that CDP-choline alone is not properly effective because it has comparatively little effect upon the proliferation of certain particularly damaging fatty acid components. In particular, administration of CDP-choline alone has little effect upon the levels of polyunsaturated compounds, principally arachidonic acid, in these cells and these polyunsaturated compounds are known to have particularly deleterious effects upon the cells. Accordingly, CDP-choline should not be used alone in the instant method. CDP-ethanolamine is more effective in suppressing the polyunsaturated fatty acids; and cytidine diphospho-N-methylethanolamine and cytidine diphospho-N,N-dimethylethanolamine may be expected to act in a manner similar to cytidine diphosphoethanolamine. However, since CDP-choline is effective in suppressing the proliferation of certain other fatty acids components which the other cytidine compounds are not effective in suppressing, it is advantageous to use a mixture of CDP-choline with one or more of the other CDP-compounds in order to effect the maximum suppression of all the various fatty acids components. The preferred therapeutic agent for use in the instant method comprises a mixture of CDP-choline and CDP-ethanolamine, it being especially preferred to use a substantially equimolar mixture.

A further reason why the use of CDP-choline alone should be avoided is that certain psychoactive effects of CDP-choline have been observed at high concentrations. Rats given a dose of $0.6\mu$ moles of CDP-choline or more become hyperactive and aggressive. An intracerebral injection of $2.5\mu$ moles per rat brain induces a near catatonic state in rats. No similar psychoactive effects are observed when CDP-ethanolamine is administered to rats by intracerebral injection. Thus, CDP-ethanolamine is accompanied by fewer undesirable side effects then CDP-choline. However, by using a mixture of the two compounds good therapeutic results can be achieved without raising the amount of CDP-choline administered to a point at which such psychoactive side effects become noticeable.

Experiments have shown that doses of CDP-choline and CDP-ethanolamine as low as $0.25\mu$ moles per rat brain are sufficient to substantially reduce the free fatty acid concentration in the brain. Typical doses found useful in practice are about 0.6 to about $1.0\mu$ moles per rat brain. The rat brain weighs approximately 1 gram, and appropriate dosages for other mammals may be calculated approximately by scaling up the dosage in porportion into the size of the brain involved, or determined by routine experiments.

Surprisingly, it has been found that the instant method is effective in suppressing free fatty acid proliferation in mammalian cells whether the therapeutic agent is administered before the onset of the injury or disease, or after the onset of the injury or disease—though in the latter case it will be appreciated that the therapeutic agent should be administered before the free fatty acid proliferation has resulted in permanent, irreversible damage to the cells. Thus, the instant method may be useful not only as a preventive measure in treating persons known to be susceptible to diseases such as strokes and heart attacks, but may also be useful as an emergency measure in treating persons who have just suffered a stroke, heart attack or similar complaint likely to produce free fatty acid proliferation. For example, physicians, paramedics and other persons who may be called upon to minister to persons immediately after they suffered strokes or heart attacks could carry a supply of the therapeutic agent of the invention and administer it as soon as they reach the stroke or heart attack victim in order to prevent the free fatty acid proliferation which is already occurring in the victim's cells, and thus prevent such free fatty acid proliferation from causing permanent and irreversible brain damage, which is often one of the most serious and disabling effects upon a person who survives a stroke or heart attack.

Factors which should be taken into account in deciding exactly which CDP-compound or mixture or compounds should be used in any particular instance include the severity of the damage to the tissue, the route of injection of the drug, the length of time which has transpired between the injury and the injection of the drug, the particular type of damage being treated and like factors.

The instant method is useful in the treatment of diseases and injuries which involve ischemic trauma, for example strokes and heart attacks. It may also be used for the treatment of other conditions wherein free fatty acid proliferation results from disease or injury, for example in heart disease and spinal cord injury. It is also believed that the instant invention will be useful in the treatment of certain diseases or injuries which, although not usually thought of as involving ischemic trauma, do involve free fatty acid proliferation, for example multiple sclerosis and Reye's syndrome.

Prior studies have shown that CDP-N-methylethanolamine and CDP-N,N-dimethylethanolamine can be incorporated into lipids and, thus, such compounds find utility in the present invention. For further detailed information on the structures of the CDP-amine compounds useful in the present invention, reference is made generally to R. W. McGilvery, "Biochemistry: A Functional Approach", Second Edition, W. B. Saunders Co., Philadelphia, Pa. (1979) and p. 603 thereof in particular.

Use of the therapeutic agents disclosed herein most suitably will be for man. It should be noted, though, that the therapeutic agents disclosed herein similarly will achieve their intended result in animals also. Thus, the treatment of mammals with the therapeutic agents disclosed herein is intended.

The following examples show how the present invention can be practiced, but should not be construed as limiting.

EXAMPLES

EXAMPLE 1

Radioactive isotope labeling was used to follow cerebral free fatty acid and lipid concentrations during ischemia and to determine the effect of CDP-choline and CDP-ethanolamine on said concentrations. Because [$^3$H] acetate, injected into rat brains, is very well incorporated into brain lipids 2 hours after injection, this radioactive compound was used for the present studies.

Four groups of rats were evaluated in this example. The first group (Control) was subjected to decapitation 2 hours after [$^3$H] acetate injection, their heads immediately frozen with liquid nitrogen and their brains removed. The concentration of cerebral lipids and free fatty acids then was determined from preparative samples by monitoring the disintegrations per minute (DPM) per rat brain of labeled cerebral lipids and free fatty acids.

The second group (Control-Ischemia) were injected, subjected to decapitation 2 hours after injection as in the Control group, but the brains were not frozen until 5 minutes after decapitation. The third group (Control-No Ischemia-Injection) received an intercerebral injection of a mixture of 0.6μ moles of CDP-choline and 0.6μ moles of CDP-ethanolamine per rat five minutes before decapitation (again, 2 hours after injection of [$^3$H] acetate). The rat brains were immediately frozen and removed. The fourth group (Ischemia-Injection) were treated the same as the third group except that the brains were not frozen until 5 minutes after decapitation.

The results obtained are given in Table 1 below. Note, that 5 rats per value in the table were tested.

TABLE 1

| | Choline Glycerophospholipids (DPM/g) | Ethanolamine Glycerophospholipids (DPM/g) | Labeled Free Fatty Acids (DPM/g) |
|---|---|---|---|
| Control | 112,800 | 31,800 | 6,400 |
| Control-Ischemia | 88,500 | 21,900 | 14,300 |
| Control-No Ischemia-Injection | 160,900 | 48,100 | 5,000 |
| Ischemia-Injection | 116,800 | 32,500 | 2,600 |

The above-tabulated results clearly show the ability of CDP-choline and CDP-ehtanolamine to substantially maintain glycerophospholipid production and suppress free fatty acid production in ischemic cerebral tissue. Note, the rapid lipid decrease and free fatty acid increase 5 minutes after ischemia (Control-Ischemia). Injection of CDP-choline and CDP-ethanolamine causes increased lipid production and attendant free fatty acid decreases in non-ischemic rat brains since the values in the third group (Control-No Ischemia-Injection) are higher than the non-ischemic rat brains with no injection of CDP-choline or CDP-ethanolamine (Control). Finally, the fourth group (Ischemia-Injection) shows that the lipid level is maintained at about the same level as is found in the non-ischemic normal rat brain and that the free fatty acid level has been somewhat lowered. With respect to tissue lipid production, CDP-choline and CDP-ethanolamine have compensated for the diminished cell energy of the ischemic cells.

EXAMPLE 2

The procedure described in Example 1 was repeated except that two different dosages of CDP-choline and CDP-ethanolamine separately were intracerebrally injected into rats before decapitation (no ischemia). The doses were 0.25 and 1.0μ moles per rat. Levels of labeled free fatty acids were determined 1, 3 and 5 minutes after injection for each dosage level. As shown in Example 1, the drop in free fatty acid level corresponds to a maintenance of cerebral lipids. The results obtained in Table 2 are based on 5 rats per value recorded.

TABLE 2

| Time (min) | FREE FATTY ACIDS (DPM/g) | | | |
|---|---|---|---|---|
| | CDP-Ethanolamine | | CDP-Choline | |
| | 0.25 | 1.0 | 0.25 | 1.0 |
| Control | 1,600 | 1,600 | 1,600 | 1,600 |
| 1 | 1,100 | 550 | 650 | 650 |
| 3 | 800 | 550 | 650 | 650 |
| 5 | 500 | 550 | 650 | 650 |

The above-tabulated results show that CDP-choline and CDP-ethanolamine are each effective in suppressing free fatty acid production in normal tissue, and by implication are effective in maintaining the level of cerebral lipids during ischemia. At the lower dose, CDP-choline appears to be more active than CDP-ethanolamine in suppressing free fatty acids. At the higher dose, both compounds appear to be equally effective; however, as noted before, higher concentrations of CDP-choline appear to induce undesirable psychoactive effects. Moreover, as the following Examples show, CDP-choline is much less effective than CDP-ethanolamine in suppressing the production of harmful polyunsaturated fatty acids, which are HETE precursors, in the brain during ischemia.

EXAMPLE 3

Rats were treated in the same manner as in Example 1, except that the therapeutic agent administered was an equimolar mixture of CDP-ethanolamine and CDP-choline containing 0.6μ moles of each compound. After isolation of the rat brains, the amounts of the various fatty acids components therein were determined by gas-liquid chromatography using a Varian Aerograph gas chromatograph the column of which was kept at a constant 180° C. The results are shown in Table 3 below; in this table, the columns headed "Amount" are in arbitrary units determined directly from the areas under the GLC-peaks.

TABLE 3

CONTENT AND COMPOSITION OF FREE FATTY ACIDS IN RAT BRAIN

| | Control | | Control-Ischemia | | CDP-Base | | Control-Ischemia | CDP-Base |
|---|---|---|---|---|---|---|---|---|
| | Amount | % | Amount | % | Amount | % | | |
| 14:0 | 2.1 | 9.7 | 3.0 | 4.7 | 1.8 | 14.0 | 1.4 | 0.9 |
| 16:0 | 7.8 | 36.2 | 13.7 | 21.4 | 1.8 | 14.0 | 1.8 | 0.2 |
| 16:1 | 1.5 | 7.1 | 3.3 | 5.2 | 1.8 | 14.0 | 2.2 | 1.2 |
| 18:0 | 3.3 | 15.3 | 17.2 | 26.9 | 2.1 | 16.4 | 5.2 | 0.6 |
| 18:1 | 2.0 | 9.2 | 9.5 | 14.9 | 1.7 | 13.3 | 4.8 | 0.9 |
| 18:2 | 3.0 | 13.8 | 6.2 | 9.6 | 2.5 | 19.5 | 2.1 | 0.8 |
| 20:4 | 1.9 | 8.6 | 11.0 | 17.2 | 1.1 | 8.6 | 5.8 | 0.6 |
| | | | | | | TOTAL | 3.0 | 0.6 |

The above results show that an equimolar mixture of CDP-choline and CDP-ethanolamine is extremely effective in suppressing free fatty proliferation during ischemia; only the 16:1 fraction was higher in the rats treated with the CDP-choline and CDP-ethanolamine mixture and then only slightly, whereas all the other fatty acid fractions were actually lower in the rats subjected to ischemia and the therapeutic agent of the invention then in the control animals which were not subjected to ischemia at all. The effectiveness of the equimolar mixture in suppressing the very large degree of proliferation of the 18:0, 18:1, and 20:4 fatty acid fractions which otherwise occurs during ischemia is especially noteworthy.

EXAMPLE 4

This example illustrates the effects of CDP-choline and CDP-ethanolamine in suppressing free fatty acid proliferation in gerbil brains, using an experimental protocol that simulates human stroke and recovery therefrom.

Gerbils (apart from a Control group) were subjected to 5 minutes of carotid artery ligation in order to induce ischemia followed by 6 minutes of reperfusion after removal of the ligatures; at the end of this 6 minute period, the animals were decapitated directly into liquid nitrogen and the frozen brains removed as in Example 1. Two groups of gerbils were separately given 1μ mole of CDP-choline or CDP-ethanolamine at 3 minutes after removal of the ligatures while a third, Control-Ischemia group received no treatment.

The fatty acid contents of the frozen brains were analyzed by gas-liquid chromatography using a Packard 12 gas-liquid chromatograph having a 183 cm. column packed with 10% Alltech CS-10 packing material. The column was temperature programmed, each run beginning with 15 minutes at 165° C., whereafter the temperature was raised at 2° C. per minute to a temperature of 205° C., then held steady at 205° C. The length of each run was 55–60 minutes. The runs were conducted using nitrogen gas as the inert carrier and a hydrogen flame detector, with the following results:

TABLE 4

| Fatty Acid | FREE FATTY ACIDS, μg/BRAIN | | | |
|---|---|---|---|---|
| | Control | Control-Ischemia | Ischemia + CDP-Choline | Ischemia + CDP-Ethanolamine |
| 14:0 | 4.8 | 5.6 | 4.2 | 6.4 |
| 16:0 | 25.2 | 37.9 | 29.3 | 26.3 |
| 16:1 | 3.1 | 5.3 | 3.9 | 7.3 |
| 18:0 | 14.2 | 47.1 | 41.3 | 32.2 |
| 18:1 | 14.8 | 30.8 | 14.5 | 19.9 |
| 18:2 | 4.7 | 37.1 | 3.2 | 8.3 |
| 20:4 | 0.9 | 30.7 | 23.0 | 13.4 |
| 22:6 | 1.5 | 6.2 | 2.4 | 2.6 |
| Total | 69.2 | 200.7 | 121.8 | 117.4 |

The above results show that the actions of CDP-choline and CDP-ethanolamine in reversing the proliferation of free fatty acids after ischemia complement each other. The CDP-choline is more effective in reversing the proliferation of 14:0, 16:1, 18:1, and 18:2 fatty acids whereas the CDP-ethanolamine is more effective in reversing the proliferation of 16:0, 18:0, and 20:4 fatty acids. The much greater efficacy of CDP-ethanolamine in reversing the 20:4 fatty acid fraction (principally arachidonic acid) is especially noteworthy since compounds derived from this fatty acid fraction are known to have particularly deleterious effects in tissues subjected to high levels thereof.

EXAMPLE 5

This example illustrates the effect of the instant therapeutic agent in reversing fatty acid proliferation in gerbil brains when the agent is administered after the onset of ischemia.

The brains of adult gerbils were radioactively labeled by injection of $^{14}C$ arachidonic acid. Two hours after the administration of the labeled acid, the gerbils (apart from the Control group) were subjected to 5 minutes of carotid artery ligation in order to induce ischemia. At the end of this 5 minute period, the ligation was terminated and the gerbils' brains allowed to reperfuse for 6 minutes before the animals were decapitated and their brains frozen in the same manner as in Example 1. One group of gerbils were not given any treatment during this reperfusion, while a second group of gerbils received, after 3 minutes reperfusion, a therapeutic agent of the invention containing 1.0μ mole each of CDP-choline and CDP-ethanolamine. Following freezing of the gerbils' brains, the inositol glycerophospholipids (IGP), choline glycerophospholipids (CGP), ethanol glycerophospholipids (EGP), tri-, di- and mono-acylglycerols (TAG, DAG and MAG respectively) and free fatty acids (FFA) components were separated and their radioactive labelling determined. The results are shown in Table 5 below.

TABLE 5

| Component | DPM/Gram Brain | | |
|---|---|---|---|
| | Control | 5 minutes ligation and 6 minutes reperfusion | 5 minutes ligation + 6 minutes reperfusion + CDP-Base |
| IGP | 8040 | 7400 | 9060 |
| CGP | 15710 | 12210 | 14960 |
| EGP | 5210 | 4910 | 5980 |
| TAG | 829 | 611 | 523 |
| DAG | 432 | 353 | 662 |
| MAG | 16 | 63 | 0 |
| FBA | 64 | 443 | 126 |

The above results show that the therapeutic agent of the invention administered after ischemia had already been caused was very effective in reducing the free fatty acid proliferation in the ischemic tissue; despite the fact that the therapeutic agent had only three minutes to take effect, it did reverse approximately 84% of the free fatty acid build-up caused by ischemia. Moreover, the therapeutic agent completely reversed the increase in mono-acylglycerols caused by the ischemia. The therapeutic agent is much more effective than either component alone.

We claim:

1. A method for substantially maintaining glycerophospholipid production by a mammalian cell and for suppressing consequent free fatty acid proliferation in said cell, said cell being susceptible to injury or disease to said mammal which causes normal glycerophospholipid production by said cell to become retarded, which method comprises: presenting said cell with a pharmaceutically effective proportion of a therapeutic agent selected from the group consisting of cytidine diphosphoethanolamine, cytidine diphospho-N-methylethanolamine, cytidine diphospho-N,N-dimethylethanolamine, mixtures thereof, and mixtures of at least one of said cytidine compounds with cytidine diphosphocholine.

2. A method according to claim 1 wherein said therapeutic agent is cytidine diphosphoethanolamine.

3. The method of claim 1 wherein said therapeutic agent is cytidine diphospho-N-methylethanolamine.

4. A method according to claim 1 wherein said therapeutic agent is cytidine diphospho-N,N-dimethylethanolamine.

5. A method according to claim 1 wherein said therapeutic agent is a mixture of cytidine diphosphocholine and cytidine diphosphoethanolamine.

6. A method according to claim 5 wherein said mixture is a substantially equimolar mixture.

7. A method according to claim 1 wherein said injury comprises ischemia.

8. A method according to claim 6 wherein said injury comprises cerebral ischemia.

9. A method according to claim 1 wherein said injury or disease comprises heart disease.

10. A method according to claim 1 wherein said disease or injury comprises stroke.

11. A method according to claim 1 wherein said disease or injury comprises a spinal cord injury.

12. A method according to claim 1, 2, 3, 4, 5, 6, 7, 8, 9, 10 or 11 wherein said mammal is human.

13. A method according to claim 1 wherein said therapeutic agent is administered after said injury or disease has already affected said mammal and normal glycerophospholipid production by said cell has become retarded.

14. A method according to claim 1 wherein said therapeutic agent is administered before said injury or disease has occurred.

15. A method according to claim 1 wherein said therapeutic agent is administered to said mammal by injection.

16. A therapeutic agent for preventing phospholipid degradation and free fatty acid proliferation, said therapeutic agent comprising a substantially isotonic injectable solution containing a therapeutically effective amount of a mixture of cytidine diphosphocholine and at least one cytidine compound selected from the group consisting of cytidine diphosphoethanolamine, cytidine diphospho-N-methylethanolamine and cytidine diphospho-N,N-dimethylethanolamine.

17. A therapeutic agent according to claim 16 containing cytidine diphosphocholine and cytidine diphosphoethanolamine.

18. A therapeutic agent according to claim 17 where said cytidine diphosphocholine and said cytidine diphosphoethanolamine are present in substantially equimolar amounts.

* * * * *